United States Patent
Liu et al.

(10) Patent No.: US 9,078,815 B2
(45) Date of Patent: Jul. 14, 2015

(54) SELF-CURE ACTIVATOR

(75) Inventors: Huaibing Liu, Dover, DE (US); Paul D. Hammesfahr, Wyoming, DE (US); Gregory Pomrink, Dover, DE (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/181,771

(22) Filed: Jul. 13, 2011

(65) Prior Publication Data

US 2013/0018123 A1    Jan. 17, 2013

(51) Int. Cl.
*A61K 6/083* (2006.01)
*A61K 6/00* (2006.01)

(52) U.S. Cl.
CPC .............. *A61K 6/0055* (2013.01); *A61K 6/0052* (2013.01); *A61K 6/083* (2013.01)

(58) Field of Classification Search
USPC ........................................................ 522/184
See application file for complete search history.

(56) References Cited

U.S. PATENT DOCUMENTS

| | | | |
|---|---|---|---|
| 4,431,421 A | 2/1984 | Kawahara et al. | |
| 4,837,271 A | 6/1989 | Brindopke | |
| 4,954,414 A | 9/1990 | Adair et al. | |
| 4,977,511 A | 12/1990 | Gottschalk et al. | |
| 5,035,621 A | 7/1991 | Gottschalk et al. | |
| 5,112,880 A | 5/1992 | Tsunekawa et al. | |
| 5,151,520 A | 9/1992 | Gottschalk et al. | |
| 5,234,970 A | 8/1993 | Kyle | |
| 5,367,002 A | 11/1994 | Huang et al. | |
| 5,530,038 A * | 6/1996 | Yamamoto et al. | 523/116 |
| 5,624,998 A | 4/1997 | Itoh et al. | |
| 5,852,136 A | 12/1998 | Green | |
| 5,866,631 A | 2/1999 | Nakagawa et al. | |
| 6,133,338 A | 10/2000 | Kimura et al. | |
| 6,489,374 B1 | 12/2002 | Baudin et al. | |
| 6,576,684 B1 | 6/2003 | Desobru et al. | |
| 6,632,877 B2 | 10/2003 | Crast et al. | |
| 6,660,784 B2 | 12/2003 | Ibaragi et al. | |
| 6,815,470 B2 | 11/2004 | Ibaragi et al. | |
| 2001/0051671 A1 | 12/2001 | Lu et al. | |
| 2002/0045678 A1 | 4/2002 | Lopez et al. | |
| 2003/0050359 A1 * | 3/2003 | Kimura et al. | 522/182 |
| 2003/0181541 A1 | 9/2003 | Wu et al. | |
| 2003/0232909 A1 | 12/2003 | Hettich | |
| 2004/0157972 A1 | 8/2004 | Yamaguchi et al. | |
| 2004/0186195 A1 | 9/2004 | Suzuki et al. | |
| 2004/0220297 A1 | 11/2004 | Bonfield et al. | |
| 2005/0009946 A1 * | 1/2005 | Oguri et al. | 522/184 |
| 2005/0124715 A1 | 6/2005 | Cohen et al. | |
| 2005/0256221 A1 | 11/2005 | Zeng et al. | |
| 2010/0298462 A1 | 11/2010 | Liu et al. | |

FOREIGN PATENT DOCUMENTS

| | | | | |
|---|---|---|---|---|
| EP | 0266220 | B1 | 5/1988 | |
| EP | 0631598 | B1 | 12/1998 | |
| EP | 0948955 | A | 10/1999 | |
| EP | 0627472 | B1 | 3/2000 | |
| EP | 1226807 | A1 | 7/2002 | |
| EP | 1391484 | A1 | 2/2004 | |
| EP | 1454921 | A1 | 9/2004 | |
| JP | 61126007 | A | 6/1986 | |
| JP | 09309811 | A | 12/1997 | |
| JP | 19990299380 | | 10/1999 | |
| JP | 2000169535 | A | 6/2000 | |
| JP | 2001122718 | A | 5/2001 | |
| JP | WO03027153 | A1 * | 4/2003 | C08F 4/68 |
| WO | 03027153 | A1 | 4/2003 | |
| WO | 2006086559 | A1 | 8/2006 | |

OTHER PUBLICATIONS

Tsuneyuki Sato & Takayuki Otsu, Chemistry & Industry, Communications to the Editor, Jan. 24, 1970.
Sato et al, Vinyl Polymerization w/a Binary System of p-Chlorbenzenediazonium Salt & Sodium Tetraphenylborate; Journal of Polymer Science: Part A:Polymer Chemistry, vol. 39, 2001.
Swift, E.J., May, KN, Wilder, AD; Journal of Prosthetics, 1998:7: 256-60.
Miller, MB et al, Reality 1999;13:1-182-7.
T.Sato et al,Die Makromolekulare Chemi;162 (1972) 9-18.
Y. Mun et al; Journal of Machromolecular Science, Chemistry (1984) A21(5) 645-660.

* cited by examiner

*Primary Examiner* — James J Seidleck
*Assistant Examiner* — Peter A Salamon
(74) *Attorney, Agent, or Firm* — Leana Levin; Douglas J. Hura; David A. Zdurne

(57) ABSTRACT

A self curing activator for chemical polymerization of the interface of a dental bonding agent and a self curing or dual curing dental cement or restorative, includes an aryl borate compound, a polymerizable monomer, an optional acidic compound, an amine compound which exhibits a catalytic action, an organic peroxide containing material, and a metal compound wherein said metal compound promotes the decomposition of the organic peroxide.

3 Claims, No Drawings

SELF-CURE ACTIVATOR

RELATED APPLICATIONS

This application claims the benefit and is a continuation of U.S. application Ser. No. 12/283,954 filed on Sep. 17, 2008, which claims the benefit and is a continuation of U.S. application Ser. No. 11/501,342 filed on Aug. 9, 2006, which claims the benefit and is a continuation of U.S. application Ser. No. 11/351,040 filed on Feb. 8, 2006, which claims the benefit of U.S. Provisional Application Ser. No. 60/651,030 filed on Feb. 8, 2005.

TECHNICAL FIELD

New Self-cure Activator is used with separate One-component Visible Light Cure Self-Etching Adhesive (1P-SEA) component, Xeno III or P&B NT type adhesives (available from Dentsply International Inc., York, Pa.) to bond cements for indirect cementation procedures (inlays/onlays/crowns/bridges/core build-up and veneers). The formulation of the prototype self-curing activator is summarized in Table 1. This system is designed to prevent dilution of the adhesive and overcome difficulties in the polymerization of a peroxide-amine cured restorative or cement in which the amine may be protonated by the acidity of the adhesive.

BACKGROUND OF THE INVENTION

Several catalysts for chemical polymerization of (meth) acrylate compounds have been identified. These systems primarily include and are not limited to the following materials:
1. A trialkylborane or a partial oxide of a trialkylborane such as tri-n-butyl borane.
2. A redox based self-curing initiator comprising a combination of an organic peroxide and a metal salt
3. A system utilizing a combination of an organic peroxide and a tertiary amine.
4. A combination of hydrogen peroxide and an Fe2+ compounds.
5. A barbituric acid, combined with a Cu2+ compound and an ionogenic halide species.
6. An aryl borate compound and an acidic compound
7. An aryl borate compound, an acidic compound and a transition metal compound An unexamined Japanese Patent Publication (Kokai No. 169535/2000) discloses a self-curing resin composition that cures at ambient temperature obtained by blending a composition of a combination of a polymerizable unsaturated compound with a radical-generating catalyst, and a polymerization initiator. The initiator consists of an organoboron compound with an acid component or with an acidic, polymerizable unsaturated compound.

The trialkylboron or the partial oxide is an effective initiator for redox polymerization however, these materials are generally pyrophoric and are chemically very unstable. This catalyst requires special packaging and requires mixing with the monomer components immediately prior to use.

The organic peroxide and metal salt or tertiary amine along with the barbituric acid systems are primarily used in various dental materials due to availability and biocompatibility. The peroxide amine systems can affect the color/shading tinting the cured product due to oxidation of the amine compound and are generally unstable due to oxygen inhibition and thermal instability of the peroxide. The barbituric acid based catalysts have been determined to exhibit difficulties with controlling the curing time and are prone to oxidation reducing their activity.

In general the aryl borates are easy to handle, do not impart color to the cured product, and exhibit acceptable stability. According to Ibaragi et al (U.S. Pat. No. 6,660,784), the difficulty with the aryl borates is that these systems do not exhibit sufficient catalytic activity.

As discussed, Chemical polymerization of vinyl or acrylate based resins via a free radical polymerization mechanism at ambient temperature is traditionally achieved using a binary, redox curing system consisting of a peroxide and an aromatic tertiary amine. On the other hand, light-activated polymerization proceeds via the generation of free radicals from the activation of a photoinitiator, usually an α-diketone, to its excited triplet state. This is followed by the reduction of the activated photoinitiator by an amine accelerator to form an intermediate excited complex (exciplex), which releases the free radicals on dissociation. There was evidence to suggest that bond strengths of resin composites to dentin were influenced by the compatibility of the polymerization modes between adhesive systems and resin composites [Swift E J, May K N, Wilder A D. Journal of Prosthodontics 1998: 7: 256-60]. A recent report further revealed that common light-cured, self-etching adhesive systems were incompatible with chemical-cured composites [Miller M B et al. Realty 1999; 13:1-182-7], to the extent that no effective bonding was achieved for some systems. However, the systems that bonded poorly to the chemically cured composites exhibited high shear bond strengths with the use of light-cured resin composites. Generally, the incompatibility of self-etching adhesives with chemical-cured resins is attributed to the reaction of the amine accelerated by the acid components of the adhesive system. More specifically, these acid components of the bonding agent protonate the tertiary aromatic amine of the organic redox catalyst in the self-curing resin composite. Subsequently, the protonated amine (quaternary aromatic amine) does not react with the peroxide to form the complex, which decomposes into radicals capable of initiating polymerization under ambient conditions. Overall, the catalyst losses efficiency and the rate and degree of functional group conversion are significantly diminished compromising the performance of the dental adhesive. Based upon this amine protonation reaction, the dental restoratives to be used in combination are limited to those of the photo-curable type only.

Although light-cured resin composites have largely superseded the use of chemical-cured composites in esthetic dental applications, chemically activated composites still have important applications in contemporary restorative dentistry. The longer working time of chemically cured composites has been adopted in the 'directed shrinkage technique' for posterior resin composite restorations. In this technique, a slow setting, chemically cured composite was used either in bulk or as a basal layer to relieve the stress developed in a restoration by the flow of the partially polymerized material. Chemically cured resins are frequently used as restorative materials in areas that are not easily penetrable by light, and as auto- or dual-curing resin cements for luting of crown and bridges, inlays and onlays along with endodontic posts. In order to facilitate the use of light curing self-etching bonding agents with dual curing or chemically curing composites, a self-curing activator is required to overcome the incompatibility of the acid containing adhesive with the amine in the redox catalyst of the chemically cured system. In the Prime&Bond NT Dual-Cure bonding system, the regular light-cure bonding agent, Prime&Bond NT is mixed with Self-Cure Activator prior to use. The Prime&Bond NT Dual-Cure exhibits excellent bond strength when bonding a dual-cure cement, e.g. Calibra, in chemical-cure mode. Since the active ingredient in Self-Cure Activator is p-toluenesulfinate, which reacts with methacrylate resins slowly on storage, the Self-Cure Activator for Prime&Bond NT is a dilute solution of p-toluenesulfinate without the presence of any polymerizable resin. Upon adding the Prime&Bond NT with the Self- Cure Activator together, the adhesive is diluted with activator. Consequently, this allows excess (atmospheric) oxygen to permeate the adhesive inhibiting free radical polymerization. Other self-curing activators contain thermally unstable peroxides, which require refrigeration to inhibit decomposition. In order to minimize this dilution effect and provide a thermally stable system, a new self-curing activator system containing polymerizable resin is required.

Several articles indicate that the binary system of tetraphenylborate (TPB) salts and organic acids could effectively initiate free radical polymerization of vinylic compounds [T. Sato et al. Die Makromolekulare Chemie 162 (1972) 9-18]. Overall, the author concluded that the reaction between the TPB ion and the proton of the acid was important in the initiating radical production. Using dimethylbenzylanilinium TPB and trichloroacetic acid (TCA), the rate of polymerization of methyl methacrylate (MMA) was found to be proportional to the square roots of the concentrations of both TPB salt and TCA, confirming that the system induced radical polymerization. The copolymerization by this system with styrene resulted in a composition curve, which was in agreement with that obtained with ordinary radical copolymerization.

In 2001, Sato et al [T. Sato et al. Journal of Polymer Science, Part A: Polymer Chemistry (2001) 4206-4213] discuss the utilization of arylborates and an aryldiazonium compound in solvent. Several polymerizable monomer systems were investigated in conjunction with differing solvent types. This study presumes that phenyl radicals are generated and proposes the mechanism for initiation based upon kinetic and EPR studies.

In 1984 Mun et al [Y. Mun et al. Journal of Macromolecular Science, Chemistry (1984) A21 (5) 645-660] discusses the polymerization of methylmethacrylate and methylacrylate using a binary system of sodium tetraphenylborate with bis(ethylacetoacetato)copper (II). This study calculated the activation energy in acetone and suggests the participation of monomer in the initiation process.

In 1983, Mun et al [Y. Mun et al. Memoirs of the Faculty of Engineering, Osaka University (1983) 24 149-159] discuss the utilization of sodium tetraphenylborate with various metal salts. This study concluded that sodium tetraphenylborate in conjunction with Cobalt and Copper salts accelerated methylmethacrylate polymerization. Manganese, Titanium and Nickel salts exhibited little or no effects on polymerization. In addition, water, crown ethers and benzoquinone inhibited the polymerization process.

In 1970 Sato et al [T. Sato et al. Chemistry & Industry, (London, UK) (1970) 4 (125)] present a method for the preparation of the N-acyloxytrialkylammonium salt of tetraphenylborate. This paper determined that the tetraphenylborate salt produced thermally decomposed to initiate methacrylate polymerization at 60° C.

U.S. Pat. No. 6,660,784B2 [K. Ibaragi, H. Kazama and M. Oguri (Tokuyama Co., Japan), issued Dec. 9, 2003] disclosed a dental catalyst for chemical polymerization comprising an acidic compound, an organic peroxide such as cumene hydroperoxide, and aryl borate compound such as sodium tetraphenylborate, but without substantially containing an amine compound. This catalyst was chemically highly stable, was easy to handle, was highly active, was less likely to be impaired by polymerization, and did not cause the cured product to be tinted or discolored, and was very useful for the dental restorative.

What was claimed is a dental catalyst for chemical polymerization comprising: an aryl borate compound, an acidic compound, an organic peroxide, with the organic peroxide containing an amount from 0.1 to 10 mols per mole of the aryl borate, without substantially containing amine compound which exhibited a catalytic action and a metal compound wherein said metal compound promotes the decomposition of the organic peroxide.

U.S. Pat. No. 5,866,631 [H. Nakagawa and H. Ohno (Tokuyama Co., Japan), issued Feb. 2, 1999] disclosed a dental primer composition capable of obtaining high adhesive strength to both dentin and enamel, as a pretreatment material for a chemically polymerizable adhesive. This composition was a dental primer composition comprising a polymerizable monomer containing an acidic group, water, aryl borate and a transition metal compound.

JP Patent 09309811 [M. Oguri, H. Kazama and T. Sato Tokuyama Soda Co. LTD., Japan Dec. 2, 1997] discloses a dental adhesive containing acidic monomers and filler with good adhesion to dentin. The preferred composition contains acid group containing monomer arylborates and fillers along with other polymerizable monomers.

JP Patent Application WO2003027153 [M. Oguri, H. Kazama, M. Kimura, K. Ibaragi, K. Fuzinami and T. Sato Tokuyama Corp., Japan Apr. 3, 2003] discloses a polymerization catalyst comprising arylborates and vanadium compounds for use in dental adhesives. The preferred composition contains acid group containing monomer arylborates and vanadium compounds in which the vanadium is in the 4+ or 5+ oxidation state.

DISCLOSURE OF THE INVENTION

Universal catalyst system used together with 1P-SEA (Xeno IV), Xeno III or Prime&Bond NT for direct and indirect bonding applications.

Bond strength of bonding agents/new SCA is comparable to or better than that of Prime&Bond NT/SCA Dual Cure adhesive.

The SCA, when combined with adhesives, provides sufficient shade stability in life of cements (does not discolor restoration), good bonding performance [Enamel≥20 MPa, Dentin≥15 MPa (Direct), Dentin≥10 MPa (Indirect)]

Low Film thickness≤15 microns

TABLE 1

Prototype Formulation of Self-Cure Activator

| Raw Material | Chemical Name | CAS # | Formulation Ranges |
|---|---|---|---|
| NaTPB | Sodium tetraphenylborate | 143-66-8 | 0.5-5.0 |
| UDMA | 2-Methyl-acrylic acid 1-methyl-2-{3,5,5-trimethyl-6-[1-methyl-2-(2-methyl-acryloyloxy)-ethoxycarbonyl amino]-hexylcarbamoyloxy}-ethyl ester | 105883-40-7 | 5-30 |
| HEMA | 2-Methyl-acrylic acid 2-hydroxy-ethyl ester | 868-77-9 | 5-30 |
| CQ | Bicyclo [2,2,1] heptane-2,3 dione, 1,1,7-trimethyl | 10373-78-1 | 0.05-1 |

TABLE 1-continued

Prototype Formulation of Self-Cure Activator

| Raw Material | Chemical Name | CAS # | Formulation Ranges |
|---|---|---|---|
| EDAB | 4-ethyl dimethylaminobenzoate | 10287-53-3 | 0.05-2 |
| BHT | Phenol, 2,6-bis (1,1-dimethylethyl-4-methyl) | 128-37-0 | 0.01-1.0 |
| Acetone | 2-Propanone | 67-64-1 | 5-95 |

PREFERRED EMBODIMENTS FOR CARRYING OUT THE INVENTION

The inventive self-cure activator (SCA) demonstrates an improvement to the existing commercial self-cure activators. The new self-cure activator finds versatile utilities to render various light cure bonding agents compatible with self-cure materials or dual-cure materials in self-cure mode.

The new SCA is contained in a single package (bottle or single unit-dose) and is mixed with a bonding agent prior to use. The new SCA is easily differentiated from the commercial Prime & Bond NT SCA in which there is no polymerizable resin monomer. The new SCA is designed to overcome dilution issues associated with Prime & bond NT SCA by incorporating resin monomers in the formulation. The unique chemistry and judicious selection of ingredients render the solution mixture storage stable.

Incorporation of the new SCA with 1P-SEA to bond self-cure (Dentsply International Inc.) Calibra yielded excellent bond strength performance using a very simple bonding procedure. This procedure is outlined as follows: Step 1: Place 1-2 drops of 1P-SEA adhesive into a mixing well. Place an equal number of drops of self-cure activator into the same mixing well. Mix contents for 1-2 seconds. Step 2: Apply the mixture to thoroughly wet all the tooth surfaces. These surfaces should remain fully wet for 20 seconds. Step 3: Remove excess solvent by gently drying for 10 seconds. Step 4: Light cure mixed adhesive/activator for 10 seconds. Step 5: Calibra placement is posted and allowed to self-cure for 15 minutes.

More specifically, this adhesive system and protocol yielded shear bond strength (SBS) values of 19.9+/−1.8 MPa on dentin and 18.8+/−2.8 MPa on enamel. In Step 3 of the procedure, light curing of the bonding agent is very important for achieving high bond strength on dentin. The self-curing initiator is not intended to cure the adhesive. As previously discussed the purpose of the of the self curing initiator is render various light cure bonding agents compatible with self-cure or dual-cure materials. In the absence of light curing the bonding agent, an SBS of only 1.4 MPa was achieved on dentin. In addition, no measurable bond strength was achieved when 1P-SEA was used directly to bond Calibra onto teeth hard tissue.

Incorporation of the new SCA with Prime &Bond NT or 1P-SEA yielded no decrease in shear bond strength after aging the SCA at 50° C. for 6 weeks. This indicates that the sodium tetraphenylborate based resin containing SCA is stable and does not polymerize or loose efficiency during storage.

Mixing the SCA with either Prime & Bond NT or 1P-SEA, the bonding mixture does not contain any organic peroxide or any transition metal compound, which were essential ingredients in the dental catalyst described in U.S. Pat. No. 6,660, 784B2 and U.S. Pat. No. 5,866,631. However, the bonding mixture does include a tertiary aromatic amine (EDAB or DMABN), whose use was excluded in U.S. Pat. No. 6,660, 784B2.

What is claimed is:

1. A self-curing activator comprising:
a one-part solution that comprises sodium tetraphenylborate, a urethane dimethacrylate, 2-hydroxy ethyl methacrylate, a photo-polymerization initiator, a stabilizer and a solvent, the self curing activator being free of organic peroxide and transition metal compounds and formulated such that, when mixed with an equal volumetric amount of a light cure dental bonding agent containing an acidic compound and a self curing or dual curing dental cement or restorative composite, results in chemical polymerization at an interface of the light cure dental bonding agent, wherein the self curing activator does not result in curing of the light cure dental bonding agent.

2. The self curing activator of claim 1 wherein the photo-polymerization initiator is selected from the group consisting of camphorquinone, 4-ethyl dimethylaminobenzoate, and combinations thereof.

3. The self curing activator of claim 1 wherein the urethane dimethacylate is 2-methyl-acrylic acid 1-methyl-2-{3,5,5-trimethyl-6-[1-methyl-2-(2-methyl-acryloyloxy)-ethoxycarbonyl amino]-hexylcarbamoyloxy}-ethyl ester.

* * * * *